(12) United States Patent
Albuquerque et al.

(10) Patent No.: US 7,888,346 B2
(45) Date of Patent: Feb. 15, 2011

(54) METHOD OF TREATING ORGANOPHOSPHOROUS POISONING

(75) Inventors: Edson X. Albuquerque, Baltimore, MD (US); Michael Adler, Bel Air, MD (US); Edna F. R. Pereira, Baltimore, MD (US)

(73) Assignee: Universtiy of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 11/575,945

(22) PCT Filed: Sep. 23, 2005

(86) PCT No.: PCT/US2005/033789

§ 371 (c)(1),
(2), (4) Date: May 23, 2007

(87) PCT Pub. No.: WO2006/036686

PCT Pub. Date: Apr. 6, 2006

(65) Prior Publication Data

US 2008/0070900 A1    Mar. 20, 2008

Related U.S. Application Data

(60) Provisional application No. 60/613,121, filed on Sep. 24, 2004.

(51) Int. Cl.
*A61K 31/55* (2006.01)
(52) U.S. Cl. ..................................... 514/215
(58) Field of Classification Search .................. 514/215
See application file for complete search history.

(56) References Cited

U.S. PATENT DOCUMENTS

| | | | |
|---|---|---|---|
| 4,550,113 A | 10/1985 | Lavretskaya et al. | |
| 4,735,953 A | 4/1988 | Lavretskaya et al. | |
| 5,480,651 A | 1/1996 | Callaway | |
| 5,795,909 A | 8/1998 | Shashoua et al. | |
| 5,939,095 A | 8/1999 | Hille et al. | |
| 6,099,863 A * | 8/2000 | Gilis et al. | 424/475 |
| 6,114,347 A | 9/2000 | Hille et al. | |
| 6,211,230 B1 * | 4/2001 | Filbert et al. | 514/454 |
| 6,261,537 B1 | 7/2001 | Klaveness et al. | |
| 6,264,917 B1 | 7/2001 | Klaveness et al. | |
| 6,331,289 B1 | 12/2001 | Klaveness et al. | |
| 6,358,941 B1 | 3/2002 | Snorrason et al. | |
| 6,458,812 B1 | 10/2002 | McKittrick et al. | |
| 6,576,636 B2 | 6/2003 | Webb et al. | |
| 6,589,504 B1 | 7/2003 | Raub et al. | |
| 6,602,902 B2 | 8/2003 | Shashoua et al. | |
| 6,610,713 B2 | 8/2003 | Tracey | |
| 6,617,361 B2 | 9/2003 | Eig | |
| 6,670,356 B2 | 12/2003 | Davis | |
| 6,680,047 B2 | 1/2004 | Klaveness et al. | |
| 6,692,767 B2 | 2/2004 | Burnside et al. | |
| 6,716,857 B2 | 4/2004 | Kim et al. | |
| 6,720,427 B2 | 4/2004 | Sanner et al. | |
| 6,756,385 B2 | 6/2004 | Sanner et al. | |
| 6,759,419 B2 | 7/2004 | Kim et al. | |
| 6,777,435 B1 | 8/2004 | Momose et al. | |
| 6,838,471 B2 | 1/2005 | Tracey | |
| 6,858,648 B2 | 2/2005 | Pan et al. | |
| 6,900,202 B2 | 5/2005 | Imoto et al. | |
| 6,906,081 B2 | 6/2005 | Hey et al. | |
| 6,919,330 B2 | 7/2005 | Vaddadi | |
| 6,964,957 B2 | 11/2005 | Abreo et al. | |
| 6,977,070 B2 | 12/2005 | Dugger, III | |
| 7,001,908 B2 | 2/2006 | Godfrey et al. | |
| 7,015,345 B2 | 3/2006 | Kawanishi et al. | |
| 7,022,725 B2 | 4/2006 | Momose et al. | |
| 7,030,081 B2 | 4/2006 | Nistri et al. | |
| 7,034,019 B2 | 4/2006 | Kukla et al. | |
| 7,034,039 B2 | 4/2006 | Oi et al. | |
| 7,038,085 B2 | 5/2006 | Rariy et al. | |
| 7,045,527 B2 | 5/2006 | Chen et al. | |
| 7,060,270 B2 | 6/2006 | Nicolau et al. | |
| 7,078,529 B2 | 7/2006 | Sanner et al. | |
| 2005/0013869 A1 | 1/2005 | Chaw et al. | |

FOREIGN PATENT DOCUMENTS

WO    WO 03/092606 A2    11/2003

OTHER PUBLICATIONS

Dawson et al., "Some adjuncts to oxime—atropine therapy for organophosphate intoxication—Their effects on acetylcholinesterase," *Biochem. Pharm.*, 28: 2211-2214 (1979).

Leaning et al., "Bloody Sunday," Report of a Medical Mission to Soviet Georgia, *Physicians for Human Rights* (1990).

(Continued)

*Primary Examiner*—Ardin Marschel
*Assistant Examiner*—Zohreh Vakili
(74) *Attorney, Agent, or Firm*—Ditthavong Mori & Steiner, P.C.

(57) ABSTRACT

A method of treating organophosphorous (OP) poisoning comprising administering to a mammal at risk for OP poisoning an OP poisoning-inhibiting amount of galantamine.

10 Claims, No Drawings

OTHER PUBLICATIONS

Samochocki et al., "Galantamine is an Allosterically Potentiating Ligand of Neuronal Nicotinic but Not of Muscarinic Acetylocholine Receptors," *JPET*, 305: 1024-1036 (2003).

Santos et al., "Low Concentrations of Pyridostigmine Prevent Soman-Induced Inhibition of GABAergic Transmission in the Central Nervous System: Involvement of Muscarinic Receptors," *JPET* 304: 254-265 (2003).

Santos et al., "Spine Density and Dendritic Branching Pattern of Hippocampal CA1 Pyramidal Neurons in Neonatal Rats Chronically Exposed to the Organophosphate Paraoxon," *Neuro Toxicology*, 25: 481-494 (2004).

Santos et al., "The Nicotinic Allosteric Potentiating Ligand Galantamine Facilitates Synaptic Transmission in the Mammalian Central Nervous System," *Mol. Pharmacol.*, 61: 1222-1234 (2002).

Shabunova et al., "Effect of cholinesterase inhibitors on the electrical excitability of the membrane of frog muscle fiber," *Fiziol Zh SSSR Im I M Sechenova*, 68:9 1223-8 (1982) (Abstract).

International Search Report issued in PCT/US05/33789 (2006).

European Office Action dated Mar. 19, 2009 for corresponding European Patent App. No. 05 812 994.1.

Kugusheva, L. I. et al., Interaction of Membrane-Bound and Solubilized Acetylcholinesterase of Human and Bovine Erythrocytes with Organophosphorus Inhibitors, journal, 1986, vol. 58, No. 3, pp. 13-18, Ukrainski Biokhimicheskii Zhurnal, Russia.

Muggleton et al., Assessment of a Combination of Physostigmine and Scopolamine as Pretreatment Against the Behavioural Effects of Organophosphates in the Common Marmoset, journal, 2003, vol. 166, No. 3, pp. 212-220, Psychopharmacology, Springer-Verlag, Germany.

Storch et al., Physostigmine, galanthamine and codeine act as 'non-competitive nicotinic receptor agonists', on clonal rat pheochromoctyoma cells, journal, 1995, vol. 290, No. 3, pp. 207-219, European Journal of Pharmacology, Elsevier Science B.V., Netherlands.

Tonkopii et al., Study of Characteristics of the Interaction of Galanthamine with Acetyl Cholin Esterase of the Mouse Brain in In-Vivo Experiments, 1976, vol. 82, No. 7, pp. 823-825.

Tonkopii V. D., Oxidative stress in the mechanism of organophosphates neurotoxicity, 2003, vol. 144, No. Suppl. 1, p. 132.

Australian Office Action for corresponding AU Application No. 2005289808, May 27, 2010.

* cited by examiner

US 7,888,346 B2

METHOD OF TREATING ORGANOPHOSPHOROUS POISONING

This patent application is a U.S. national phase application of International Patent Application No. PCT/US2005/033789, filed Sep. 23, 2005, which claims the benefit of U.S. Provisional Patent Application No. 60/613,121, filed Sep. 24, 2004, the contents of which are incorporated herein by reference in their entireties.

STATEMENT OF GOVERNMENT SUPPORT

The invention described herein was made, at least in part, with funding from the U.S. Army under Grant No. DAAD19-02-D-0001, with funding from the U.S. Army Medical Research and Development Command under Contract No. DAMD17-95-C-5063, with funding from the National Institutes of Health under U.S. Public Health Service Grant No. NS25296, and with funding from the National Institute of Environmental Health Sciences under Training Grant No T32 ES07263. Therefore, the United States of America has certain rights in the invention.

TECHNICAL FIELD OF THE INVENTION

The present invention relates to a method of treating organophosphorous poisoning in an animal, in particular a mammal, specifically a human.

BACKGROUND OF THE INVENTION

Organophosphorous compounds (OPs), due to their physical state and high lipophilicity, rapidly penetrate and accumulate in the central nervous system (CNS). OP poisoning of military personnel on the battlefield and of common citizens in the event of a terrorist attack with nerve gas, for example, has caused an increase in concern for public and governmental authorities around the world in recent years. In addition, increased demands for food and ornamental crops have resulted in an increase in the use of toxic anti-cholinesterase (anti-ChE)-based pesticides, including OPs such as parathion and malathion, in developed and developing countries. This has resulted in an increase in the accidental poisoning of farmers and gardeners.

It has long been known that the main toxic effects of OPs and other anti-ChE agents result from the inhibition of the enzyme ChE, which is responsible for the inactivation of the neurotransmitter acetylcholine (ACh) in the CNS and peripheral nervous system (PNS), thereby abnormally increasing and prolonging muscarinic and nicotinic cholinergic responses. Unfortunately, current methods to treat or prevent the toxic effects of OPs are still far from acceptable, particularly in the event of acute exposure to nerve agents that are highly absorbable and readily accessible to the brain.

Reversible ChE inhibitors, such as pyridostigmine bromine (PB), physostigmine, and huperzine, have been tested as antidotal therapy against OP poisoning. PB has been used as a preventive treatment by soldiers in the field. While it is a powerful anti-ChE agent, its action is mostly limited to the PNS, due to the fact that it is a charged molecule that hardly penetrates the CNS. Therefore, PB does not effectively confer protection of brain ChE against nerve gases. Physostigmine is more effective than PB, but less safe. Therefore, there currently is no method of protecting the brain from irreversible ChE inhibition by OPs. Rather, those individuals, who have been exposed to OP, have been treated post-exposure with antimuscarinic agents, such as atropine, ChE reactivators, such as oximes, e.g., pyridine-2-aldoxime (2-PAM), and anticonvulsants, e.g., Diazepam.

In view of the above, it is an object of the present invention to provide a method of treating OP poisoning. This and other objects and advantages, as well as additional inventive features, will become apparent from the detailed description provided herein.

BRIEF SUMMARY OF THE INVENTION

The present invention provides a method of treating OP poisoning. The method comprises administering to a mammal at risk for OP poisoning an OP poisoning-inhibiting amount of galantamine, whereupon the mammal is protected from OP poisoning upon exposure to an OP.

DETAILED DESCRIPTION OF THE INVENTION

The present invention is predicated, at least in part, on the surprising and unexpected discovery, that a tertiary alkaloid, such as galantamine, can be administered to an animal, in particular a mammal, specifically a human, at risk of OP poisoning to protect the animal from OP poisoning. While galantamine is a weaker ChE inhibitor as compared to PB and physostigmine, it is a non-charged molecule and, therefore, has the ability to pass through the blood-brain barrier. Galantamine also functions as an allosteric potentiating ligand (APL) of nicotinic receptors (nAChRs), and is able to "rescue" some nicotinic receptors from desensitization. This property is important in the context of OP poisoning when excess ACh induces massive desensitization of nAChRs.

In view of the above, the present invention provides a method for antidotal therapy of OP poisoning. The method comprises administering to a mammal at risk for OP poisoning an OP poisoning-inhibiting amount of galantamine, whereupon the mammal is protected from OP poisoning upon subsequent exposure to an OP. The galantamine can be administered to the mammal before or after exposure to an OP. If galantamine is administered before exposure, the method further comprises subsequently administering to the mammal an effective amount of an antimuscarinic agent, such as atropine. If galantamine is administered after exposure, the method further comprises administering an effective amount of an antimuscarinic agent, such as atropine, after exposure to an OP and prior to or simultaneously with an OP-poisoning inhibiting effective amount of galantamine. Preferably, the antimuscarinic agent and galantamine are administered as soon as possible after exposure to an OP in order to maximize the effectiveness of the post-treatment. Depending on the timing of subsequent administration of the antimuscarinic agent and galantamine in relation to the time of exposure to an OP, this embodiment can have therapeutic effects as well.

A mammal is at risk for OP poisoning if it is currently exposed to or is at risk of being exposed to a level of OP that is sufficiently high to poison the mammal. Such risk exists for military personnel on the battlefield, common citizens in the event of a terrorist attack with nerve gas, and farmers and gardeners who work with food and ornamental crops treated with anti-ChE-based pesticides.

An amount of galantamine is an "OP poisoning-inhibiting amount" or an "effective amount" when it is sufficient to diminish significantly, preferably completely, the detrimental effects of exposure to OPs as evidenced by signs of ill health, including but not limited to, any peripheral and central hypercholinergic signs of OP intoxication, such as hypersecretion, muscle contraction, respiratory difficulties, convulsion, or behavioral abnormalities. Amounts of galantamine that are sufficient to inhibit OP poisoning can be determined in accordance with dosage range-finding techniques as are known in the art. For example, an optimal dose can be determined by a skilled clinician in a clinical setting or in the field. Generally, optimal doses are determined by incrementally altering an initial dose until the optimum effect under the circumstances is achieved. Doses of galantamine, such as galantamine hydrobromide, ranging from about 5 mg/kg to about 8 mg/kg effectively prevent toxicity and lethality induced by lethal doses of the nerve agents soman and sarin when 10 mg/kg atropine, such as atropine sulfate, are also administered. Galantamine is an effective antidotal therapy when used acutely for up to about 1 hr before or up to about 5 min after exposure to an OP.

Galantamine is commercially available from Hande Industry & Trade Holdings Co., Ltd., Shenzhen, China, among others. Desirably, the galantamine is suitable for administration to an animal, such as a mammal, in particular a human, as a pharmaceutical composition. The formulation of pharmaceutical compositions is known in the art (see, e.g., *Remington: The Science and Practice of Pharmacy*, Mack Pub. Co.). Galantamine is currently available as a pharmaceutical composition under the name Reminyl™ (Janssen-Cilag, Ltd., UK) for the treatment of Alzheimer's disease.

The galantamine can be administered by any suitable route of administration as is known in the art. Preferred routes of administration include, but are not limited to, oral and intramuscular. The route of administration will depend, in part, upon the circumstances of risk of exposure. For example, oral administration can be preferred for pre-treatment of a predicted exposure, as in the case of farm workers and other individuals who handle OP insecticides on a regular basis, e.g., daily, whereas intramuscular administration can be preferred for post-treatment of military personnel on the battlefield and civilians exposed to OPs, such as in the context of a terrorist attack.

If the mammal is exposed to an OP after administration of galantamine, preferably, an effective amount of an antimuscarinic agent, such as atropine, is administered to the mammal as soon as possible after exposure to the OP. The antimuscarinic agent can be administered by any suitable route. Intramuscular administration is normally preferred. An amount of an antimuscarinic agent, such as atropine, is an "effective amount" when it is sufficient to inhibit, preferably prevent, any adverse effects of exposure to OP. An effective amount of an antimuscarinic agent can be determined in accordance with dosage range-finding techniques as are known in the art. For example, an optimal dose can be determined by a skilled clinician in a clinical setting or in the field. Generally, optimal doses are determined by incrementally altering an initial dose until the optimum effect under the circumstances is achieved. As mentioned above, about 10 mg/kg is the most effective dose of atropine, such as atropine sulfate, when galantamine, such as galantamine hydrobromide, is administered in a dose of about 5 mg/kg to about 8 mg/kg.

Atropine is available from Sigma Chemical Co. (St. Louis, Mo.). Desirably, the atropine or other antimuscarinic agent is suitable for administration to an animal, such as a mammal, in particular a human, as a pharmaceutical composition (see, e.g., Remington, supra).

EXAMPLES

The following examples serve to illustrate the present invention but are not intended to limit its scope in any way.

Example 1

This example demonstrates the effectiveness of pre-treatment with galantamine in a mammal subsequently exposed to an OP.

Galantamine (4-10 mg/kg) was administered (intramuscularly) to guinea pigs (young males weighing 300-420 g) 30 min prior to or 5 min after exposure of the guinea pigs to 1.5-2.0× the 50% lethal dose (LD50) of soman (42 or 56 µg/kg subcutaneous injection) or sarin (63 or 73.5 µg/kg subcutaneous injection). Atropine sulfate (6-16 mg/kg) was administered (intramuscularly) to some of the guinea pigs 1-2 min after administration of the nerve agent soman or sarin. Simultaneously with or subsequently to (e.g., within about 4 min) atropine administration, some of the guinea pigs received galantamine (intramuscularly). Control guinea pigs received galantamine (4-8 mg/kg), atropine (6-16 mg/kg), a combination thereof, or saline. Survival and body weight were followed for at least one week.

Galantamine was found to protect the guinea pigs against lethal doses of soman or sarin. A treatment consisting of 5-8 mg/kg galantamine and 10 mg/kg atropine fully protected the guinea pigs against toxicity and lethality induced by 1.5× LD50s of soman and sarin. Not only did galantamine fully protect the guinea pigs against death but, shortly after OP injection, the guinea pigs did not show any peripheral and central hypercholinergic signs of OP intoxication, such as hypersecretion, muscle contraction, respiratory difficulties, convulsion, or behavioral abnormalities, and, during the observation period of up to 1-2 weeks, they showed no signs of ill health. Those guinea pigs that received soman or sarin followed by atropine sulfate all presented life-threatening symptoms within 10-20 min and were euthanized as per the IACUC-approved protocol for animal care and handling.

In the first 24 hr, all guinea pigs receiving OP showed 5-10% weight loss; however, in the following days, the guinea pigs gained weight. With galantamine doses giving partial protection, some guinea pigs showed signs of OP intoxication. These guinea pigs had life-threatening symptoms within hours or days after the OP challenge and were euthanized as per the IACUC-approved protocol for animal care and handling. Such guinea pigs showed different degrees of OP toxicity and did not recover their body weights. However, after 3-4 days following the OP challenge, no further deaths were recorded. Control guinea pigs receiving either galantamine (up to 8 mg/kg) or atropine (6-10 mg/kg) or the mixture of the two protecting agents showed no loss of body weight or other untoward effects or signs of intoxication.

When the guinea pigs were euthanized by decapitation following deep anesthesia with $CO_2$, blood samples (obtained by cardiac puncture) and whole brains were removed and immediately frozen in dry ice for subsequent analysis of cholinesterase inhibition and galantamine levels. Initial measurements indicated that intramuscular injection of 8 mg/kg galantamine resulted in plasma and brain concentrations of the agent of approximately 1-3 µM, which are similar to the concentrations of galantamine observed in the plasma of humans treated with doses of galantamine clinically recommended for treatment of Alzheimer's disease. The concentrations of galantamine in the brain are sufficient to prevent desensitization of nAChRs by rising levels of ACh resulting from OP-induced irreversible inhibition of cholinesterases. Cholinesterase inhibition in the brain was in the range of 20% to <1% from the highest to the lowest measured concentrations of galantamine. Even when brain cholinesterase inhibition was negligible, galantamine still arrested OP-induced toxicity.

The brains of those guinea pigs that were successfully protected from OP poisoning by pre-or post-treatment with galantamine were compared to those of control guinea pigs morphometrically using Fluoro Jade B staining. Neuronal viability and structures were very similar in the brains of control and (galantamine+atropine)-treated, OP-challenged animals.

Example 2

This example demonstrates the effectiveness of post-treatment with galantamine in a mammal, which has been exposed to an OP.

Soman (42 μg/kg) was administered (subcutaneously) to guinea pigs (young males weighing 300-420 g). After 1 min, atropine (10 mg/kg) was administered (intramuscularly) to the animals. Simultaneously with or subsequently to (e.g., 4 min later) atropine administration, galantamine (8-10 mg/kg) was administered (intramuscularly) to the animals. Administration of 8-10 mg/kg galantamine within 5 min of administration of soman provided 100% protection. In contrast, administration of 6 mg/kg galantamine within 5 min of administration of soman only provided approximately 35% survival. In the first 24 hrs, all guinea pigs showed about a 5% weight loss; however, in the following days, the guinea pigs gained weight at the same rate as control animals that were not challenged with OPs.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. A method of treating organophosphorous (OP) poisoning by administering to a mammal at risk for OP poisoning therapeutically effective amounts of galantamine and an antimuscarinic agent according to a treatment regimen selected from the group consisting of:
   1) administering galantamine prior to OP exposure and an antimuscarinic agent after OP exposure,
   2) administering galantamine after OP exposure simultaneously with antimuscarinic agent, and
   3) administering antimuscarinic agent after OP exposure and galantamine after administration of the antimuscarinic agent.

2. The method of claim 1, wherein the galantamine is administered orally or intramuscularly.

3. The method of claim 1, wherein galantamine is administered up to about 1 hour before or up to about 5 minutes after exposure to an OP.

4. The method of claim 1, wherein the antimuscarinic agent is atropine.

5. The method of claim 1, wherein the antimuscarinic agent is atropine sulfate and wherein the galantamine is galantamine hydrobromide.

6. The method of claim 1, wherein the OP exposure is a lethal exposure level of up to about 1.5×LD50 and said galantamine preserves neuronal structures in the brain of the treated mammal.

7. The method of claim 1, wherein the galantamine is administered up to about 1 hour before exposure to OP.

8. The method of claim 1, wherein the galantamine is administered about 30 minutes before exposure to OP.

9. The method of claim 1, wherein
   regimen 1) further comprises administering galantamine hydrobromide up to about 1 hour before OP exposure and administering atropine sulfate within about 2 minutes after OP exposure,
   regimen 2) further comprises administering galantamine hydrobromide after OP exposure simultaneously with atropine sulfate and within about 2 minutes of OP exposure, and
   regimen 3) further comprises administering atropine sulfate within about 2 minutes after OP exposure and administering galantamine after administration of the atropine sulfate and within about 5 minutes of OP exposure.

10. The method of claim 9, wherein the galantamine is administered orally or intramuscularly.

* * * * *

UNITED STATES PATENT AND TRADEMARK OFFICE
CERTIFICATE OF CORRECTION

PATENT NO.       : 7,888,346 B2
APPLICATION NO.  : 11/575945
DATED            : February 15, 2011
INVENTOR(S)      : Edson X. Albuquerque, Michael Adler and Edna F. R. Pereira Page 1 of 1

It is certified that error appears in the above-identified patent and that said Letters Patent is hereby corrected as shown below:

On the TITLE Page, under:

(73) Assignee: University of Maryland, Baltimore, (Baltimore, MD) (US)

ADD AND INSERT AS A SECOND ASSIGNEE:

--and
The Government of the United States as represented by The Secretary of the Army, U.S. Army Medical Research Institute of Chemical Defense (Fort Detrick, MD) (US)--

Signed and Sealed this
Twenty-fourth Day of July, 2012

David J. Kappos
*Director of the United States Patent and Trademark Office*